US00PP27804P3

(12) United States Plant Patent
van Kleinwee

(10) Patent No.: US PP27,804 P3
(45) Date of Patent: Mar. 21, 2017

(54) ***PETUNIA* PLANT NAMED 'PEHY0008'**

(50) Latin Name: *Petunia hybrida*
Varietal Denomination: PEHY0008

(71) Applicant: SYNGENTA PARTICIPATIONS AG, Basel (CH)

(72) Inventor: Theodorus Cornelis van Kleinwee, Enkuizen (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/757,314

(22) Filed: Dec. 16, 2015

(65) Prior Publication Data

US 2016/0198611 P1 Jul. 7, 2016

Related U.S. Application Data

(60) Provisional application No. 62/099,638, filed on Jan. 5, 2015.

(51) Int. Cl.
*A01H 5/02* (2006.01)

(52) U.S. Cl.
USPC ..... Plt./356.18

(58) Field of Classification Search
USPC ..... Plt./356.18
CPC ..... A01H 5/02
See application file for complete search history.

*Primary Examiner* — Kent L Bell
(74) *Attorney, Agent, or Firm* — Dale Skalla

(57) ABSTRACT

A new *Petunia* plant named 'PEHY0008' particularly distinguished by its purple flowers with large white center, dark green foliage, good branching, a semi-trailing to mounding habit, and floriferous throughout the season.

1 Drawing Sheet

Latin name of the genus and species of the plant claimed: *Petunia hybrida.*

Varietal denomination: 'PEHY0008'.

BACKGROUND OF THE NEW PLANT

The present invention comprises a new *Petunia*, botanically known as *Petunia hybrida*, and hereinafter referred to by the variety name 'PEHY0008'.

'PEHY0008' is a product of a planned breeding program. The new cultivar has large, purple flowers with white center, dark green foliage, good branching, a semi-trailing to mounding habit, and is floriferous throughout the season.

'PEHY0008' originated from a hybridization made in October 2009 in a controlled breeding environment in Enkhuizen, Netherlands. The female parent was the unpatented proprietary plant designated 'G1506-1' with a light rose flower color, a small flower size, and a rather strong vigor and trailing plant habit The male parent of 'PEHY0008' was an unpatented proprietary plant identified as 'H9260-1' with violet-blue flower color with a white center, an upright plant habit, and relatively late flowering.

The resulting seeds were sown in February 2010. 'PEHY0008' was selected as a single flowering plant within the progeny of the stated cross May 25, 2010 in a greenhouse in Enkhuizen, Netherlands.

The first act of asexual reproduction of 'PEHY0008' was accomplished when vegetative cuttings were propagated from the initial selection in June 2010 in a controlled environment in Enkhuizen, Netherlands.

BRIEF SUMMARY OF INVENTION

Horticultural examination of plants grown from cuttings of the plant initiated in September 2010 in Angers, France and continuing thereafter, has demonstrated that the combination of characteristics as herein disclosed for 'PEHY0008' are firmly fixed and are retained through successive generations of asexual reproduction.

'PEHY0008' has not been observed under all possible environmental conditions. The phenotype may vary significantly with variations in environment such as temperature, light intensity, and day length.

A Plant Breeder's Right for this cultivar was applied for in the European Community Plant Variety Office (CPVO) on Jun. 27, 2014, No. 2014/1716. 'PEHY0008' has not been made publicly available more than one year prior to the filing of this application.

The following traits have been repeatedly observed and are determined to be basic characteristics of the new variety. The combination of these characteristics distinguishes this *Petunia* as a new and distinct variety.

BRIEF DESCRIPTION OF THE PHOTOGRAPHS

The accompanying photographic drawing shows typical flower and foliage characteristics of 'PEHY0008' with colors being as true as possible with an illustration of this type.

Figure 1:
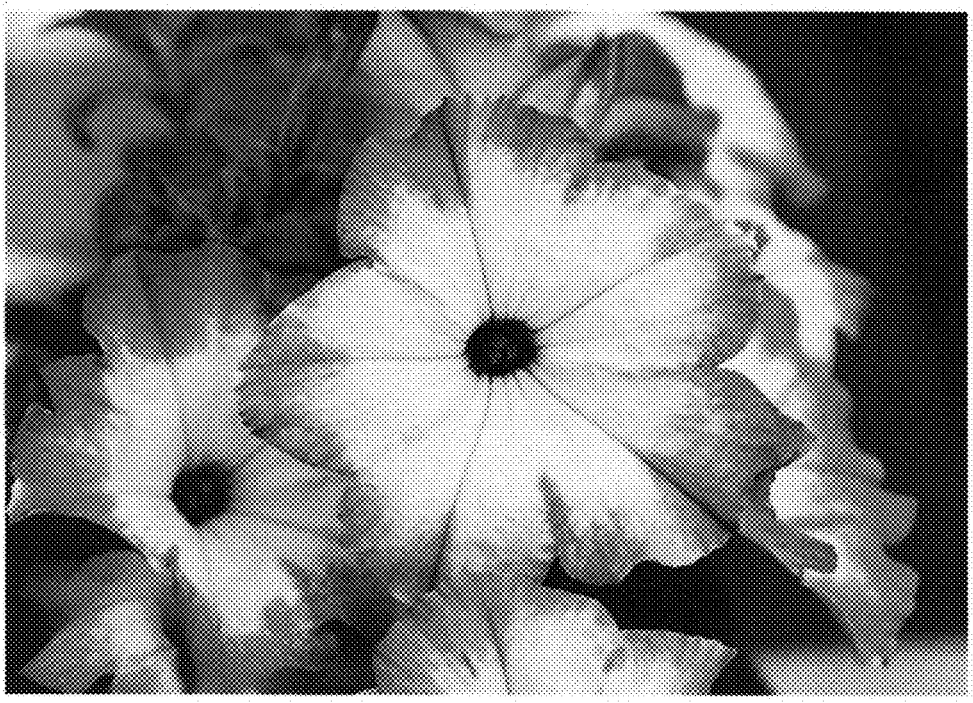
Figure 2:
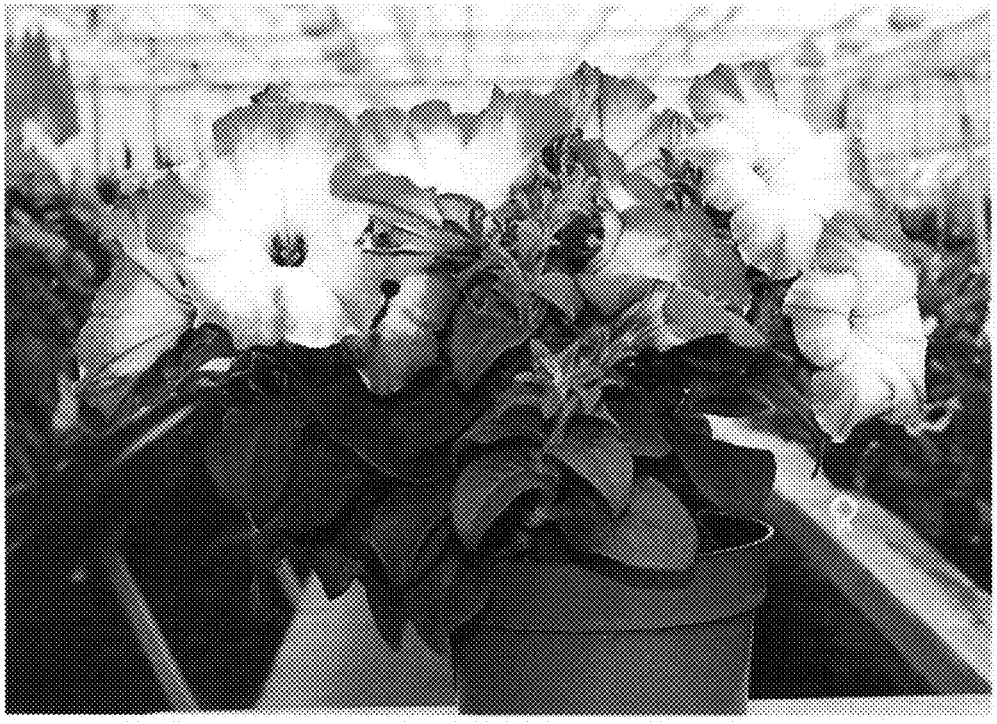

The photographic drawing shows in FIG. 2. a flowering plant of the new variety and in FIG. 1. a close-up of the flowers.

DETAILED BOTANICAL DESCRIPTION

The plant descriptions and measurements were taken in late September 2014 from plants grown for breeding purposes in a greenhouse in Enkhuizen, Netherlands. The plants had been planted around Jul. 10, 2014. They were approximately 11 weeks of age and growing in 19 cm containers. They had been cut back a few weeks before the observations.

The aforementioned photographs were taken in April 2014 from plants growing in a greenhouse trial in Andijk, Netherlands. These plants were approximately 12-13 weeks of age.

Color references are made to The Royal Horticultural Society Colour Chart (R.H.S.) 2001.

TABLE 1

DIFFERENCES BETWEEN THE NEW VARIETY 'PEHY0008' AND A SIMILAR VARIETY

| | 'PEHY0008' | 'FORTUNIA PURPLE PICOTEE' |
|---|---|---|
| Flower color pattern: | Bluish pink with large white center | Deep violet N79B and White margin |
| Aspect of leaves: | Tips reflexed | Leaf blade flat |
| Earliness: | Rather early flowering | Rather late flowering |

Plant:

*Form, growth and habit.*—Mounding to semi-trailing habit, good branching, big flowers.

*Plant height.*—13 cm.

*Plant height (inflorescence included).*—17 cm.

*Plant width.*—26 cm.

*Fragrance.*—Slight.

Roots:

*Number of days to initiate roots.*—About 15 days at about 22 degrees C.

*Number of days to produce a rooted cutting.*—21-24 days at 22 degrees C.

*Type.*—Fine, fibrous, free branching.

*Color.*—Near RHS N155B.

Foliage:

*Arrangement of leaves.*—Simple, opposite, sometimes decussate.

*Immature leaf, color upper surface.*—RHS 137B.

*Immature leaf, color lower surface.*—RHS 137C, somewhat more yellowish.

*Mature leaf, color, upper surface.*—RHS 137A.

*Mature leaf, color lower surface.*—Near RHS 143B.

*Length.*—5.5 cm.

*Width.*—3.5 cm.

*Shape.*—Ovate.

*Base shape.*—Obtuse.

*Apex shape.*—Acute or obtuse.

*Margin.*—Entire.

*Texture, upper surface.*—Both hirsute and glandular hair.

*Texture, lower surface.*—Both hirsute and glandular hair.

*Color of veins, upper surface.*—RHS 144B.

*Color of veins, lower surface.*—RHS 144B.

*Petiole color.*—RHS 144B.

*Length.*—0.4-0.5 cm.

*Diameter.*—0.3 cm.

*Texture.*—Pubescent, with longer hairs along the edges.

Stem:

*Quantity of main branches per plant.*—4-6.

*Color of stem.*—RHS 143A.

*Length of stem.*—10-12 cm.

*Diameter.*—0.4 cm.

*Length of internodes.*—3-3.5 cm.

*Texture.*—Densely covered with glandular hairs and hirsute hair.

*Color of pedicels.*—RHS 143A.

*Length.*—3 cm.

*Diameter.*—0.2-0.3 cm.

*Texture.*—Hirsute, much glandular hair.

Inflorescence:

*Type of inflorescence.*—Single flowers, emerging from the upper nodes of the stem.

*Blooming habit.*—Continuous flowering throughout the summer months.

*Start of flowering.*—8 weeks from planting rooted cuttings.

*Lastingness of individual blooms on the plant.*—Up to 14 days in greenhouse, depending on temperature.

*Quantity of flowers per plant.*—About 10-15.

*Fragrance.*—Slight scent.

Bud (just before opening):

*Color: from the base to the top.*—RHS 79B to RHS 79C at the top, lower part RHS 79D, with a little green, RHS 145B; veins of RHS 92A color over the whole length.

*Length.*—5-5.5 cm.

*Width.*—0.8-2 cm at the top.

*Shape.*—Oblong.

Immature flower:

*Diameter.*—6.5-7.3 cm.

*Color upper surface.*—Slightly more pink than RHS N78A.

*Color lower surface.*—RHS N78C to white, corolla tube RHS N81B.

Mature flower:

*Shape.*—Salver-shape, with funnel shape base, formed by 5 fused petals.

*Horizontal diameter.*—About 7.5 cm.

*Vertical diameter.*—4 cm.

*Overall flower color.*—Purple margin with very large white, or nearly white 'eye', no distinct veins.

*Color upper surface.*—RHS N78B or RHS N78C near margin; center RHS N155A or whiter.

*Color lower surface.*—RHS N78C to RHS N78D.

*Petal apex shape.*—Mucronulate, slightly twisted.

*Petal base shape.*—Fused.

*Petal margin.*—Entire.

*Waviness of petals margin.*—Weak to medium.

*Petal lobation.*—Weak to medium.

*Petal texture, upper surface.*—Glabrous, papillose.

*Petal, texture, lower surface.*—Papillose, mainly glabrous.

*Corolla tube, color inside.*—RHS N81A with black veins.

*Corolla tube, color outside.*—RHS N81B with black veins.

*Corolla tube length.*—3 cm.

*Corolla tube, diameter.*—1.1 cm.

*Corolla tube texture, outside.*—Rough with glandular hair.

Calyx:

*Form.*—5 sepals in a whorl, fused at the base.

*Color upper surface.*—RHS 137B.

*Color lower surface.*—RHS 137C to RHS 137D.

*Length.*—2.2 cm.

*Width.*—0.4-0.5 cm.

*Sepal, shape.*—Ensiform.

*Apex shape.*—Acute.

*Base.*—Fused.

*Margins.*—Entire.

*Texture upper surface*.—Hirsute.
*Texture lower surface*.—Hirsute with shorter hair than on upper surface.

Reproductive organs:
*Gyneocium*.—
*Pistil*.—1.
*Length*.—2.2 cm.
*Style color*.—RHS 145C.
*Style length*.—2 cm.
*Stigma color*.—RHS 144A.
*Stigma shape*.—Discoid.
*Ovary color*.—RHS 144A.

Androecium:
*Stamens, quantity*.—1.
*Color of filaments*.—RHS 155C mainly; at upper end purple, RHS 84B.
*Length filaments*.—2.6 cm.
*Anther color*.—RHS 202B.
*Anther length*.—0.1 cm.
*Anther shape*.—Elliptical.
*Color of pollen*.—RHS 202B, but slightly more bluish.
*Pollen amount*.—Plenty.

Fertility/seed set: Has not been observed on this hybrid.

Disease/pest resistance: Has not been observed on this hybrid.

What is claimed is:

1. A new and distinct variety of *Petunia* plant named 'PEHY0008' substantially as illustrated and described herein.

* * * * *